United States Patent
Vitale et al.

(10) Patent No.: US 7,318,504 B2
(45) Date of Patent: Jan. 15, 2008

(54) ADJUSTING MECHANISM FOR A PROSTHETIC

(75) Inventors: Thomas N. Vitale, Oakdale, CA (US); David A. Hill, Patterson, CA (US)

(73) Assignee: Thermal Techniques Inc., Modesto, CA (US)

( * ) Notice: Subject to any disclaimer, the term of this patent is extended or adjusted under 35 U.S.C. 154(b) by 114 days.

(21) Appl. No.: 10/998,091

(22) Filed: Nov. 24, 2004

(65) Prior Publication Data

US 2005/0109563 A1    May 26, 2005

Related U.S. Application Data

(60) Provisional application No. 60/525,289, filed on Nov. 25, 2003.

(51) Int. Cl.
*F16D 69/00* (2006.01)

(52) U.S. Cl. .................... 188/265; 188/322.15; 623/43

(58) Field of Classification Search ................. 188/31, 188/60, 283, 285, 316, 320, 265, 322.15; 623/21.18, 36, 37, 40, 43, 45, 47, 50, 56, 623/22.19, 22.28
See application file for complete search history.

(56) References Cited

U.S. PATENT DOCUMENTS

| | | | |
|---|---|---|---|
| 5,704,945 A | 1/1998 | Wagner et al. | 623/44 |
| 5,957,981 A | 9/1999 | Gramnas | 623/47 |
| 6,855,170 B2 * | 2/2005 | Gramnas | 623/49 |
| 2004/0186591 A1 * | 9/2004 | Lang | 623/39 |

* cited by examiner

*Primary Examiner*—Pam Rodriguez
(74) *Attorney, Agent, or Firm*—John P. Wooldridge

(57) ABSTRACT

An adjusting mechanism alters the heel height on a prosthetic foot, and works independently of any articulating ankle joint or foot style, without changing the original dynamic alignment of a prosthetic leg. In a two chamber hydraulic closed system—a fluid material is allowed to flow through the two chambers by use of pistons that push the fluid material equally from one chamber to another until the desired heel height is obtained. Once the correct position is obtained, the ports are closed by use of a push button stop, which closes the ports and stops all transfer of fluid between the ports holding the heel in position during use.

23 Claims, 4 Drawing Sheets

ADJUSTING MECHANISM FOR A PROSTHETIC

This application claims priority to U.S. Provisional Patent Application Ser. No. 60/525,289, titled: "Heel Height Adjusting Mechanism For A Prosthetic Foot," filed Nov. 25, 2003, incorporated herein by reference.

BACKGROUND OF THE INVENTION

1. Field of the Invention

The present invention relates to prosthetics, and more specifically, it relates to an adjusting mechanism for a prosthetic.

2. Description of Related Art

A variety of adjustable prosthesis joints are known; however, they are generally expensive to manufacture, complex and larger than desirable.

For example, U.S. Pat. No. 5,957,981 claims an adjustable prosthesis joint to set the angular relation between an attachment socket for connecting the joint to a cooperating body member and a prosthesis detail, the prosthesis joint comprising a housing; a chamber disposed in the housing; an intermediate wall fixed within the chamber to subdivide the chamber into at least two communicating chamber portions, wherein the cross-section of the chamber is curved so that the wall subdivides the chamber into two cylindrical curved chamber portions; an adjustable valve provided in a valve housing in connection to the wall, wherein the adjustable valve is movable between a closed position and an open position; a flow medium to communicate between the chamber portions through the valve; at least two pistons wherein each piston is movably disposed in one of the two chamber portions and the pistons are interconnected to and are adapted to be uniformly displaced in relation to the wall under flow of the flow medium through the valve in the open position between the chambers.

Another example of a prostheses joint that is complex, expensive to manufacture and large is found in U.S. Pat. No. 5,704,945, which claims a brake-action knee joint for a leg prosthesis, comprising: an upper prosthetic part; a lower prosthetic part; a joint pin which includes a rotary piston and which is connected in a torsionally rigid fashion to the upper part of the joint; a rocker which forms a central part of the joint, the rocker having an extension-side end fixed to a rocker pin lying parallel, ventrally and distally with respect to the joint pin and having a flexion-side end, wherein the rocker surrounds the joint pin; and a braking device activated by foot loading, which includes a closed, fluid-filled displacer chamber; a valve plunger having an open position and a closed position; a valve-plunger spring; and a first adjusting device mounted on the lower prosthetic part of the joint and connected to the valve plunger; wherein the displacer chamber concentrically surrounds the joint pin over its circumference, at least partially and is arranged in an associated end of the central part of the joint, wherein the rotary piston divides the displacer chamber into an extension chamber and a flexion chamber, which are connected to one another by way of an oil line which can be completely or partially closed by the valve plunger; and wherein the valve plunger is mounted in the central part of the joint in such a way as to be displaceable counter to the action of the valve-plunger spring pushing it into its open position and, when the central part of the joint is pivoted in the direction of flexion about the rocker pin, is pushed into its closed position by the adjusting device.

It is desirable to provide a simplified, relatively inexpensive and small mechanism for adjusting the angular position of a prosthetic. The present invention provides such a mechanism.

SUMMARY OF THE INVENTION

It is an object of the present invention to provide an adjusting mechanism for adjusting the relative position of a prosthetic device with respect to another device, attachment or human or animal body part.

It is another object to provide a method for fabricating an adjusting mechanism.

These and other objects will be apparent to those skilled in the art based on the disclosure herein.

The invention is an adjusting mechanism for adjusting the position of a prosthetic. In the exemplary embodiment, the adjusting mechanism alters the heel height on a prosthetic foot, and will work independently of any articulating ankle joint or foot style, without changing the original dynamic alignment of a prosthetic leg. Each individual patient as necessary can accomplish this, after delivery of a prosthesis.

The exemplary embodiment is designed as an infinitely adjustable heel height positioning unit and fixture alignment tool used in artificial legs. This is accomplished m the adjusting mechanism of the present invention by means of a two chamber hydraulic closed system wherein a fluid material is allowed to flow through the two chambers by means of pistons which push the fluid material equally from one chamber to another until the desired heel height is obtained. Once the correct position is obtained, the ports are closed by means of a push button stop, which closes the ports and stops all transfer of fluid between the ports holding the heel in position during use. An embodiment of the present adjusting mechanism comprises: a first integral support structure having a series of openings with a first piston chamber on a first end and a second piston chamber on a second end; a first piston operatively emplaced within said first piston chamber; a second piston operatively emplaced within said second piston chamber; a flow medium located within said series of operatively connected openings; a valve operatively emplaced within said first integral support structure, wherein said valve is configured to have a first position that provides a clear path between said first piston chamber and said second piston chamber, wherein said valve is configured to have a second position that prevents a clear path between said first piston chamber and said second piston chamber, and a second integral support structure comprising means for connecting to and mechanically communicating with said first integral support structure, wherein when said valve is in said first position, said first piston and said second piston will alternately extend and retract allowing said first integral support to rotate with respect to said second integral support, wherein when said valve is in said second position, said first piston and said second piston will be locked in place and said first integral support will not rotate, but will be locked with respect to said second integral support. The valve may comprise a push button valve that may comprise a valve shaft and with at least one seal that may comprise a center o-ring and two outside back-up o-rings. Each of said first piston and said second piston include at least one seal that may be a high-pressure O-ring of, e.g., polyurethane. The adjusting mechanism may further comprise a back-up o-ring. Each of said first piston and said second piston may comprise hardened tool steel. The push button valve is emplaced within said first through-hole, wherein said push button valve is configured to have a first position relative to said first through hole, wherein said first position provides a clear path between said second passage and said third passage, wherein said push button valve is configured to have a second position relative to said first through hole, wherein said second position prevents a clear path between said second passage and said third passage. The flow medium may be selected from a group consisting of a fluid material and grease. The flow medium can be pressurized at a pressure within a range from about 25 psi to about 140 psi, and specifically at about 85 psi.

The adjusting mechanism may further comprise means for repeatably sealing, opening and resealing said series of operatively connected openings, wherein series of operatively connected openings can be refilled with said flow medium if necessary. The means for repeatably sealing, opening and resealing said series of operatively connected openings may comprise (i) a first high pressure plug removably attached to said first flow medium injection port, and (ii) a second high pressure plug removably attached to said a second flow medium injection port.

BRIEF DESCRIPTION OF THE DRAWINGS

The accompanying drawings, which are incorporated into and form a part of the disclosure, illustrate embodiments of the invention and, together with the description, serve to explain the principles of the invention.

DETAILED DESCRIPTION OF THE INVENTION

Figure 1:
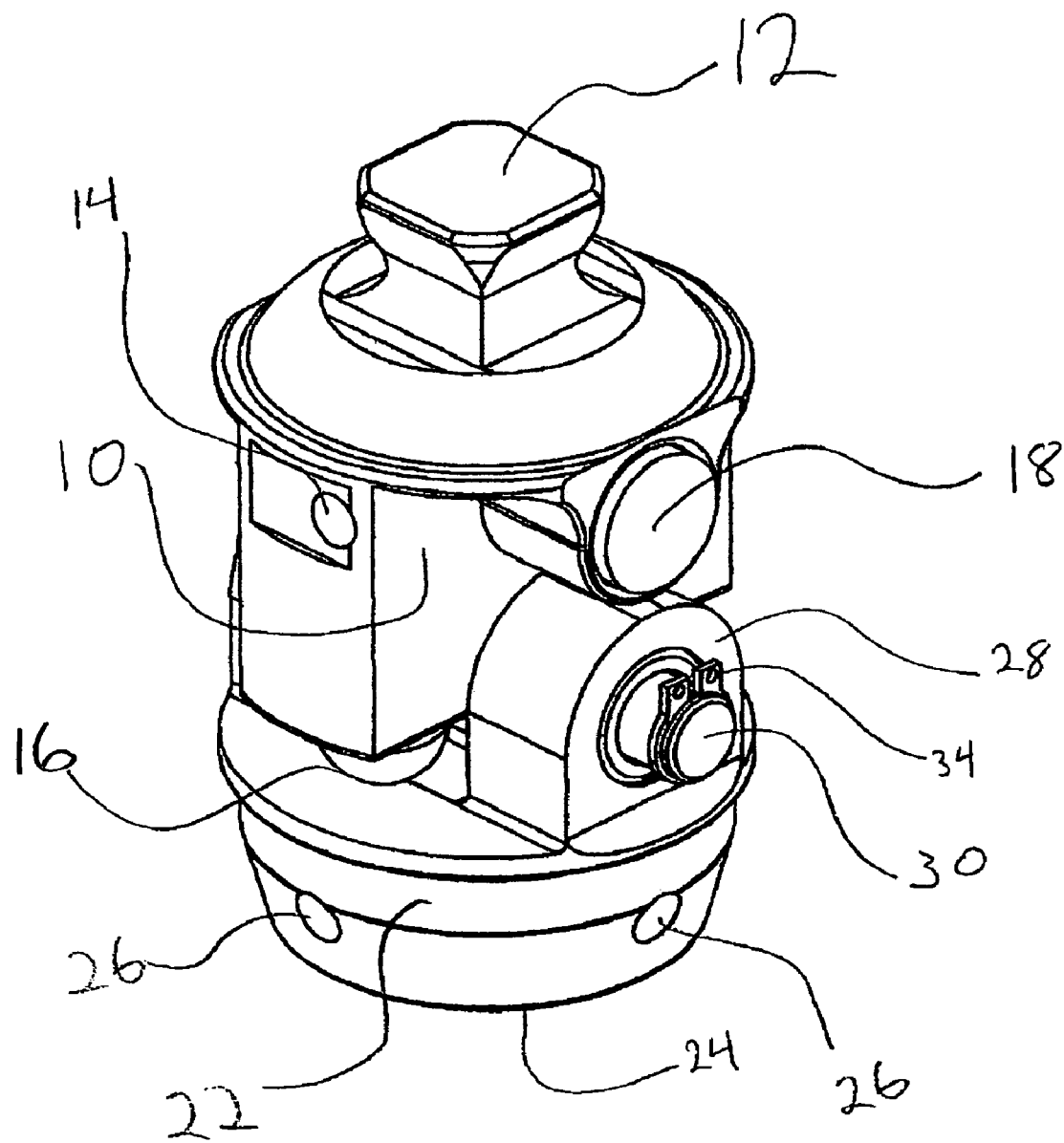
FIG. 1 shows a perspective view of an exemplary embodiment of the present invention.
Figure 2A:
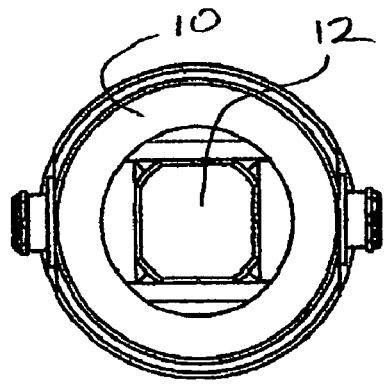
FIGS. 2A-4F show a series of views of an exemplary embodiment of the present invention.
Figure 2E:
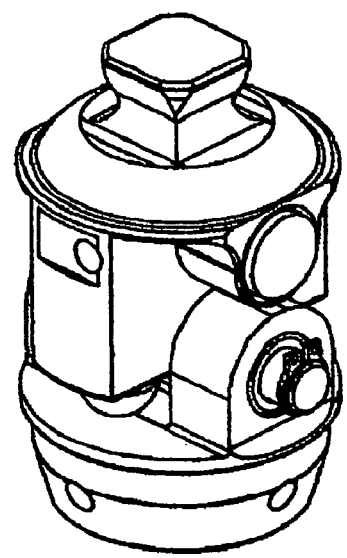
Figure 2B:
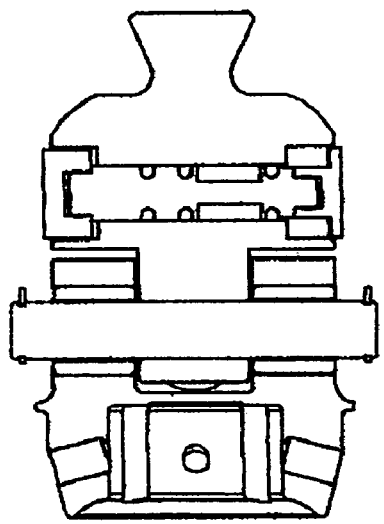
Figure 2D:
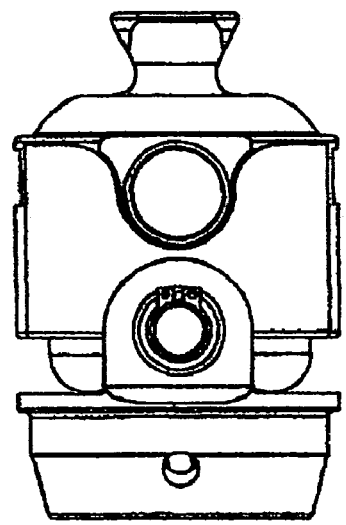
Figure 2C:
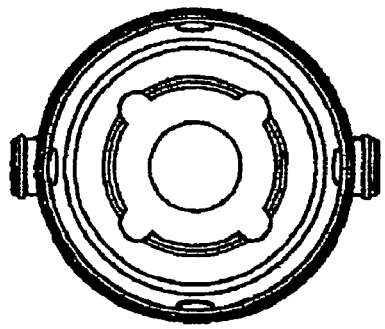
Figure 3A:
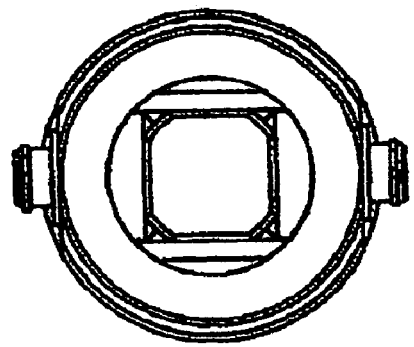
Figure 3E:
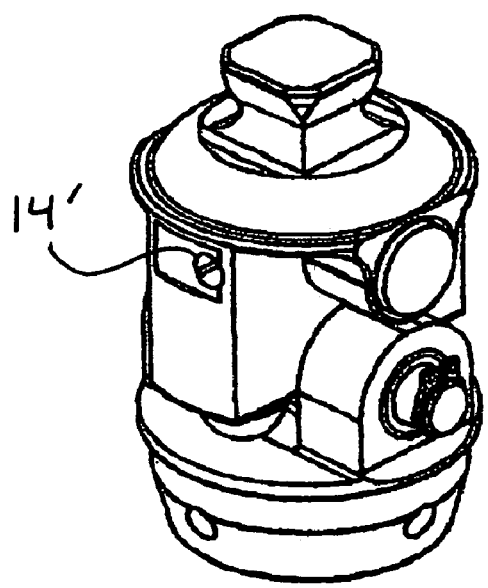
Figure 3B:
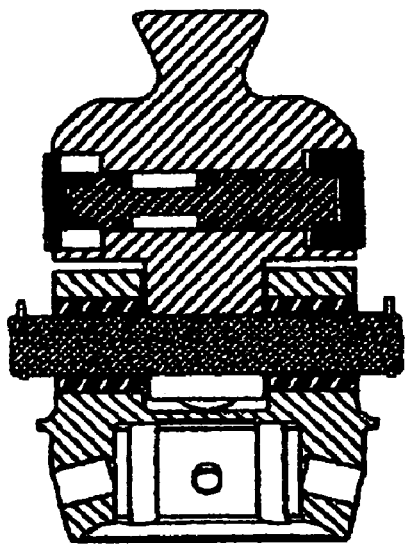
Figure 3D:
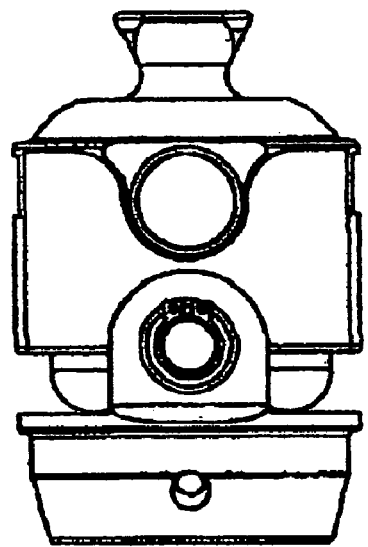
Figure 3C:
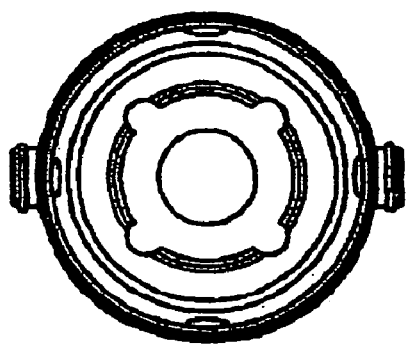
Figure 4A:
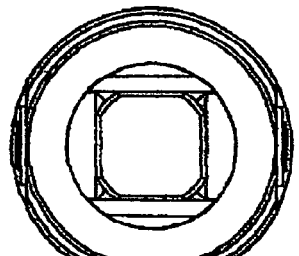
Figure 4F:
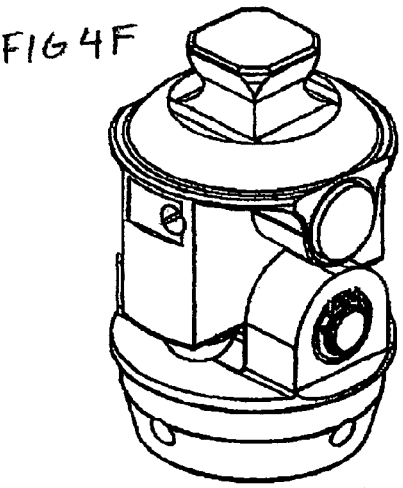
Figure 4B:
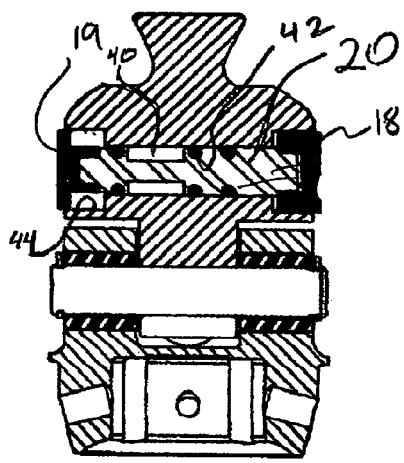
Figure 4D:
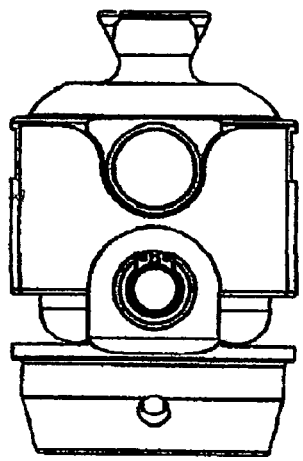
Figure 4E:
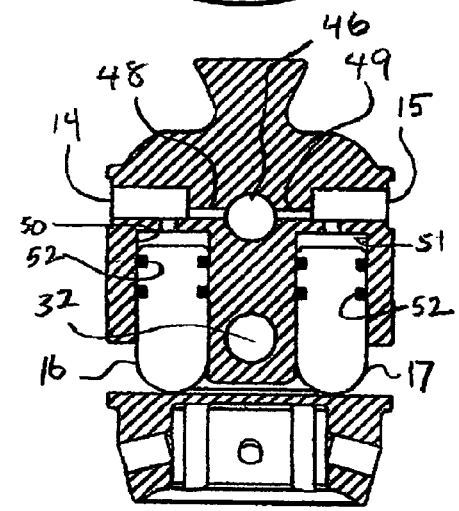
Figure 4C:
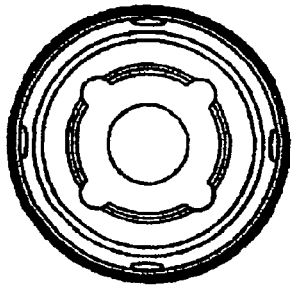

FIG. 1 shows a perspective view of an embodiment of the present invention. Upper support unit 10 includes a standardized male connector 12, which is well known in the art. A grease insertion port 14 is shown on one side of upper support unit 10. Another grease insertion port 15 (not shown) is on the opposite side of the grease insertion port 14. A set screw can be sealed in place in each grease insertion port after the desired amount of grease has been inserted into the internal valve and cylinder system discussed below. A piston 16 is shown protruding from the bottom of the upper support unit 10. Another piston 17 (not shown) is located parallel to and on the opposite side of the upper support unit 10 from piston 16. A valve control button 18 is shown on one side of upper support unit 10. This button 18 is connected to a valve control shaft 20 that is internal to the upper unit 10 and thus not shown in this figure.

Referring again to FIG. 1, a lower support unit 22 includes a standardized female connector 24 (not visible in this view). Set screws, placed in openings 26, are usable to secure the unit to another connector similar to connector 12 of a unit to which the present invention may be attached. Lower unit 22 includes a first bridge portion 28 through which a rotation axis pin 30 may be passed. A second bridge portion 29 is located on the opposite side of the lower unit 22 parallel to the first bridge portion 28. Upper unit 10 includes a rotation through hole 32, which provides a clear path for the pin 30 to pass. When assembled, pin 30 is passed through bridge 28, hole 32 and bridge 29 and secured in place with securing mechanisms 34 and 35 (not shown).

FIGS. 2A-4F show a series of views of an exemplary embodiment of the present invention. FIG. 4B shows a side cut-away view of the assembly. Note the valve control buttons 18 and 19 connected to valve control shaft 20. Shaft 20 includes a port 40 and seals 42. Upper unit 10 includes a bored out diameter 44 on one end that is large enough that valve control button 19 may be pushed in toward the center of the assembly. This will cause the valve control shaft 20 to slide within a through hole 46 within which shaft 20 is located, such that port 40 is aligned with valve ports 48 and 49 shown in FIG. 4E. FIG. 4E is a side cut-away view of the assembly perpendicular to the view of FIG. 4B. Thus, shaft 20 is located in hole 46 of FIG. 4E. As discussed above with reference to FIG. 1, a volume of grease is forced into grease entry ports 14 and 15, which ports are subsequently sealed. The volume of grease fills the internal area, which is under vacuum, in this embodiment. Pistons 16 and 17 are located within cylinders 50 and 51 respectively and include seals 52. When button 19 is pressed up against the stop of bored out hole 44, shaft 20 slide such that port 40 aligns with ports 48 and 49. In this position, which is referred to herein as the "unlocked" position, the pistons can move up and down in the cylinders. For example, when piston 16 moves up in cylinder 50, the constant volume of grease forces piston 17 down in cylinder 51. When button 18 is pushed, it forces shaft 20 to move such that port 40 is no longer aligned with ports 48 and 49. In this position, which is referred to herein as the "locked" position, force applied to either piston will not move that piston because the grease cannot flow within the system.

The assembly can be attached to a prosthetic, placed in the unlocked position, the angle is adjusted between the upper unit and the lower unit, and then the assembly is locked. In practice, e.g., a practitioner or user could attach the assembly to a prosthetic (prosthesis) and the end user could place it in the unlocked position. The user could then adjust the angle between the upper unit 10 and the lower unit 22 so that the assembly was comfortable. The user could then place the assembly in the locked position to hold it in the desired alignment.

The present invention can be made in a variety of ways. Examples of suitable materials are metals (e.g., aluminum, titanium) and plastics. The invention can be machined or cast The following is a description of a machining method. In the first step, the raw material is placed into a CNC Lathe. Material is removed to form a straight diameter and a spherical radius on one end of a shaft. A parting tool separates the part from the bar stock. In the second step, the part is placed into a fixture in a CNC Milling machine and is held by the straight section that was produced in the first step. Material is removed by use of an end mill cutting tool to create two straight sections, leaving a solid body of material extending from one side of the round stock to the other side. Two holes are then drilled from the top of the part to form the piston chambers. The bottoms of the holes are then flattened by means of a drill-type cutting device. A hole is then drilled on the flat surface at the bottom of the piston chambers to connect to a hole to be drilled perpendicular to the piston chamber at a later time. A boring tool is then used to size each piston hole to a +0.0015/−0.000 nominal diameter of the mating piston.

In the third step, the part is then moved in the fixture so that it is held horizontally to be trimmed and gripped by the flat sections machined in the second step. A hole is then drilled into the body of the part to form the chamber used to insert the grease into the finished product. A second hole is then drilled to flatten the bottom of the first hole drilled in this step. This first hole crosses the hole drilled in the bottom of the piston chamber hole described in the second step to allow a connection between these two chambers. A small hole is drilled at the bottom of the grease filled hole to a depth to enter a hole to be drilled perpendicular to this hole in a later step. A high-pressure port tool is then used to create a seal surface for a high-pressure plug (14' in FIG. 3E) to be installed during final assembly of the finished product The port hole is then tapped to connect with the high pressure plug described above. The part is then turned 180 degrees and this process is repeated.

In the fourth step 4, the part is then moved in a fixture and held perpendicular to the grease fill holes, and timed by the flat sections machined in the second step. A hole is drilled through the material at the end furthest from the spherical radius end of the part machined in step 1, to be referred to as hole 1. A second hole is then drilled through the material closer to the spherical end of the part, to be called hole 2. An end mill cutting tool is then used to remove the remaining rough stock below the spherical radius of the part, creating a raised radial section of material around hole number 2. A counter bore is then milled into the raised boss of material surrounding hole number 2. A larger counter bore is then machined into the flat section of material in which hole number 1 was drilled. A corner radius cutting tool is then used to radius the top edge of the counter bore surrounding hole number 2, the edge of the bottom of the counter bore and hole number 2, and the bottom of the counter bore and hole number 1. A reamer is then used to size hole number 1 to a diameter of +0.000/−001 of the diameter of a mating pin to be installed during final assembly. A high precision reamer is then used to size hole number 2 to a diameter of +or −0.0003 of a specific size to be used by an additional tool to be used later. A roller burnishing tool is then used to provide a specific diameter of +or −0.0005 to a mating part to be used in final assembly in hole number 2. This tool also provides a finish to be used as a sealing surface for a series of o rings to be used in the final assembly of the part; additionally the tool provides for a smooth edge of the hole drilled in the bottom of the grease fill holes, drilled in the third step, connecting the grease fill holes to hole number 2. The part is then turned over 180 degrees and the above procedures with the exception of drilling, reaming and burnishing of holes number 1 and 2, are repeated.

In the fifth step, the part is then moved in the fixture so that the diameter turned in step number 1 is facing upward. The part is held and timed by the flat sections milled in step number 2. An end mill cutting tool is then used to cut angular flat sides in a square pattern parallel and perpendicular to the flat sides milled in step 2 and wherein the sides of the square pattern are angled so that the top of the square has larger sides than the bottom. In the last step, the part is then placed in the fixture horizontally so that holes number 1, and 2 described in step number 4, are perpendicular to the surface being held, and is timed by the flats milled in step 2. An end mill cutting tool is then used to cut the bottom end of the part farthest from the spherical radius end in an angular pattern to allow clearance for a mating part to be used in the final assembly. A radius cutting end mill tool is then used to radius the top edge of the profile cut described above. The part is turned over 180 degrees and the radius tool is then run on the opposite side of the profile cut described above. The part is then cleaned and deburred.

The foregoing description of the invention has been presented for purposes of illustration and description and is not intended to be exhaustive or to limit the invention to the precise form disclosed. Many modifications and variations are possible in light of the above teaching. The assembly is characterized as having an upper unit and a lower unit, which characterization is intended to show the relative positions of the two units, but is not intended to limit the usable orientation of the assembly, e.g., the assembly can be inverted, or used in another orientation without departing from the scope of the invention. The embodiments disclosed were meant only to explain the principles of the invention and its practical application to thereby enable others skilled in the art to best use the invention in various embodiments and with various modifications suited to the particular use contemplated.

We claim:

1. An adjusting mechanism, comprising:
   a first integral support structure having a series of operatively connected openings with a first piston chamber on a first end and a second piston chamber on a second end;
   a first piston operatively emplaced within said first piston chamber;
   a second piston operatively emplaced within said second piston chamber;
   a flow medium located within said series of operatively connected openings;
   a valve comprising a valve shaft, a port and at least one seal around said valve shaft, wherein said valve is operatively emplaced within said first integral support structure, wherein said valve is configured to have a first position that provides a clear path between said first piston chamber and said second piston chamber, wherein said valve is configured to have a second position that prevents a clear path between said first piston chamber and said second piston chamber, and
   a second integral support structure comprising means for connecting to and mechanically communicating with said first integral support structure, wherein when said valve is in said first position, said first piston and said second piston will alternately extend and retract allowing said first integral support to rotate with respect to said second integral support, wherein when said valve is in said second position, said first piston and said second piston will be locked in place and said first integral support will not rotate, but will be locked with respect to said second integral support, wherein said series of operatively connected openings further comprises:
   a first port connected by a first passage to said first piston chamber;
   a first through-hole configured for emplacement of said valve, wherein said first through-hole is connected by a second passage to said first port;
   a second port connected by a third passage to said first through-hole; and
   a fourth passage connected between said second piston chamber and said second port.

2. The adjusting mechanism of claim 1, wherein said valve comprises a push button valve.

3. The adjusting mechanism of claim 2, wherein said first port comprises a first flow medium injection port and said second port comprises a second flow medium injection port.

4. The adjusting mechanism of claim 3, wherein said first integral support structure further comprises a second through-hole configured to receive and rotate on an axel.

5. The adjusting mechanism of claim 3, wherein said push button valve is emplaced within said first through-hole, wherein said push button valve is configured to have a first position relative to said first through hole, wherein said first position provides a clear path between said second passage and said third passage, wherein said push button valve is configured to have a second position relative to said first through hole, wherein said second position prevents a clear path between said second passage and said third passage.

6. The adjusting mechanism of claim 5, wherein said flow medium is selected from a group consisting of a fluid material and grease.

7. The adjusting mechanism of claim 5, wherein said flow medium within said series of openings has a pressure within a range from about 25 psi to about 140 psi.

8. The adjusting mechanism of claim 5, wherein said flow medium within said series of openings has a pressure of about 85 psi.

9. The adjusting mechanism of claim 1, further comprising means for repeatably sealing, opening and resealing said series of operatively connected openings, wherein series of operatively connected openings can be refilled with said flow medium if necessary.

10. The adjusting mechanism of claim 9, wherein said means for repeatably sealing, opening and resealing said series of operatively connected openings comprises (i) a first high pressure plug removably attached to said first flow medium injection port, and (ii) a second high pressure plug removably attached to said a second flow medium injection port.

11. The adjusting mechanism of claim 4, wherein said means for connecting to and mechanically communicating with said first integral support structure comprises a first axel support, a second axel support and an axel operatively emplaced through said first axel support, said second through-hole and said second axel support, wherein when said push button valve is in said first position, said first piston and said second piston will alternately extend and retract allowing said first integral support to rotate about said axel with respect to said second integral support, wherein when said push button valve is in said second position, said first piston and said second piston will be locked in place and said first integral support will not rotate, but will be locked with respect to said second integral support.

12. The adjusting mechanism of claim 1, wherein said at least one seal comprises a center o-ring and two outside back-up o-rings.

13. The adjusting mechanism of claim 1, wherein said first integral support structure further comprises a means for connecting to a first element that is not a part of said adjusting mechanism, wherein said second integral support structure further comprises means for connecting to a second element that is not a part of said adjusting mechanism.

14. The adjusting mechanism of claim 13, wherein at least one of said first element or said second element comprises a prosthetic.

15. The adjusting mechanism of claim 1, wherein each of said first piston and said second piston includes at least one seal.

16. The adjusting mechanism of claim 15, wherein said at least one seal comprises a high-pressure O-ring.

17. The adjusting mechanism of claim 16, wherein said high-pressure O-ring comprises polyurethane.

18. The adjusting mechanism of claim 15, further comprising a back-up ring.

19. The adjusting mechanism of claim 15, wherein each of said first piston and said second piston comprises hardened tool steel.

20. The adjusting mechanism of claim 1, wherein each of said first piston chamber and said second piston chamber comprises substantially straight side walls and wherein each of said first piston and said second piston have substantially straight sides.

21. The adjusting mechanism of claim 1, wherein said second integral support structure comprises a base portion including means for connecting to a second element that is not a part of said adjusting mechanism.

22. The adjusting mechanism of claim 1, wherein said adjusting mechanism forms a prosthetic joint.

23. A adjusting mechanism, comprising:
a push button valve;
a first integral support structure including:
a series of operatively connected openings comprising:
a first piston chamber;
a first flow medium injection port connected by a first passage to said first piston chamber;
a first through-hole configured for emplacement of said push-button valve, wherein said first through-hole is connected by a second passage to said first flow medium injection port;
a second flow medium injection port connected by a third passage to said first through-hole; and
a second piston chamber connected by a fourth passage to said second flow medium injection port;
a second through-hole configured to receive and rotate on an axel; and
means for connecting said first integral support structure to a first element that is not a part of said adjusting mechanism;
a first piston operatively emplaced within said first piston chamber, wherein said first piston includes at least one seal;
a second piston operatively emplaced within said second piston chamber, wherein said second piston includes at least one seal;
wherein said push button valve is emplaced within said first through-hole, wherein said push button valve is configured to have a first position relative to said first through hole, wherein said first position provides a clear path between said second passage and said third passage, wherein said push button valve is configured to have a second position relative to said first through hole, wherein said second position prevents a clear path between said second passage and said third passage,
a flow medium located within said series of operatively connected openings; and
means for repeatably sealing, opening and resealing said series of operatively connected openings, wherein said series of operatively connected openings can be refilled with said flow medium if necessary;
a second integral support structure comprising:
a base portion including means for connecting to a second element that is not a part of said adjusting mechanism;
a first axel support; and
a second axel support; and
where said axel is operatively emplaced through said first axel support, said second through-hole and said second axel support, wherein when said push button valve is in said first position, said first piston and said second piston will alternately extend and retract allowing said first integral support to rotate about said axel with respect to said second integral support, wherein when said push button valve is in said second position, said first piston and said second piston will be locked in place and said first integral support will not rotate, but will be locked with respect to said second integral support.

* * * * *